(12) United States Patent
Govari et al.

(10) Patent No.: US 11,490,957 B2
(45) Date of Patent: *Nov. 8, 2022

(54) SPECTRAL SENSING OF ABLATION

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Joseph Thomas Keyes, Glendora, CA (US); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 542 days.

This patent is subject to a terminal disclaimer.

(21) Appl. No.: 16/435,681

(22) Filed: Jun. 10, 2019

(65) Prior Publication Data
US 2019/0290358 A1  Sep. 26, 2019

Related U.S. Application Data

(63) Continuation of application No. 14/585,135, filed on Dec. 29, 2014, now Pat. No. 10,314,650, which is a
(Continued)

(51) Int. Cl.
*A61B 18/14* (2006.01)
*A61B 5/00* (2006.01)
(Continued)

(52) U.S. Cl.
CPC ........ *A61B 18/1492* (2013.01); *A61B 5/0036* (2018.08); *A61B 5/0075* (2013.01);
(Continued)

(58) Field of Classification Search
None
See application file for complete search history.

(56) References Cited

U.S. PATENT DOCUMENTS 5,137,355 A  8/1992  Barbour et al.
5,368,015 A  11/1994  Wilk
(Continued)

FOREIGN PATENT DOCUMENTS

CN  1132470 A  10/1996
CN  101132730 A  2/2008
(Continued)

OTHER PUBLICATIONS

Real time assessment of RF cardiac tissue ablation with optical spectroscopy; by Demos et al.; pub. Sep. 15, 2008 / vol. 16, No. 19/ Optics Express 15286 (Year: 2008).*
(Continued)

*Primary Examiner* — Katherine L Fernandez
*Assistant Examiner* — Michael S Kellogg
(74) *Attorney, Agent, or Firm* — Etan S. Chatlynne; Calderon Safran & Cole P.C.

(57) ABSTRACT

A method for tissue assessment includes ablating tissue at a site within a body of a living subject using an invasive probe applied to the site. At a first stage in ablation of the tissue, first measurements are made of scattered light intensities from the site at a plurality of different wavelengths. At a second stage in the ablation of the tissue, subsequent to the first stage, second measurements are made of the scattered light intensities from the site at the plurality of different wavelengths. Progress of the ablation is assessed by computing different, respective measures of change in the scattered light intensities at the different wavelengths occurring between the first and second measurements, and comparing the respective measures.

20 Claims, 7 Drawing Sheets

Related U.S. Application Data continuation-in-part of application No. 13/716,517, filed on Dec. 17, 2012, now abandoned, which is a continuation-in-part of application No. 12/816,492, filed on Jun. 16, 2010, now abandoned.

(51) Int. Cl.
  *A61B 18/00* (2006.01)
  *A61B 5/02* (2006.01)
  *A61B 17/00* (2006.01)

(52) U.S. Cl.
  CPC .......... *A61B 5/0084* (2013.01); *A61B 5/6852* (2013.01); *A61B 5/6869* (2013.01); *A61B 5/0086* (2013.01); *A61B 5/02007* (2013.01); *A61B 5/4836* (2013.01); *A61B 2017/00061* (2013.01); *A61B 2017/00066* (2013.01); *A61B 2018/00357* (2013.01); *A61B 2018/00577* (2013.01); *A61B 2018/00642* (2013.01); *A61B 2018/00738* (2013.01); *A61B 2018/1407* (2013.01)

(56) References Cited

U.S. PATENT DOCUMENTS

| | | |
|---|---|---|
| 5,391,199 A | 2/1995 | Ben-Haim |
| 5,441,483 A | 8/1995 | Avitall |
| 5,443,489 A | 8/1995 | Ben-Haim |
| 5,464,983 A | 11/1995 | Wang |
| 5,497,769 A | 3/1996 | Gratton et al. |
| 5,558,091 A | 9/1996 | Acker et al. |
| 5,687,730 A | 11/1997 | Doiron et al. |
| 5,782,237 A | 7/1998 | Casciani et al. |
| 5,944,022 A | 8/1999 | Nardella et al. |
| 5,983,126 A | 11/1999 | Wittkampf |
| 5,987,351 A | 11/1999 | Chance |
| 6,172,499 B1 | 1/2001 | Ashe |
| 6,177,792 B1 | 1/2001 | Govari et al. |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 7,001,383 B2 | 2/2006 | Keidar |
| 7,306,593 B2 | 12/2007 | Keidar et al. |
| 7,662,152 B2 | 2/2010 | Sharareh et al. |
| 7,918,850 B2 | 4/2011 | Govari et al. |
| 7,920,906 B2 | 4/2011 | Goode et al. |
| 8,123,745 B2 | 2/2012 | Beeckler et al. |
| 8,147,484 B2 | 4/2012 | Lieber et al. |
| 8,211,102 B2 | 7/2012 | Paul et al. |
| 8,417,323 B2 | 4/2013 | Uzunbajakava et al. |
| 2002/0038116 A1 | 3/2002 | Lee et al. |
| 2002/0041723 A1 | 4/2002 | Ronnekleiv et al. |
| 2002/0156380 A1 | 10/2002 | Feld et al. |
| 2004/0006333 A1 | 1/2004 | Arnold et al. |
| 2004/0015065 A1 | 1/2004 | Panescu et al. |
| 2004/0181135 A1 | 9/2004 | Drysen |
| 2005/0010095 A1 | 1/2005 | Stewart et al. |
| 2005/0034819 A1 | 2/2005 | Brown et al. |
| 2005/0038419 A9 | 2/2005 | Arnold et al. |
| 2006/0122587 A1* | 6/2006 | Sharareh ................ A61B 18/24 606/11 |
| 2006/0155193 A1 | 7/2006 | Leonardi et al. |
| 2006/0184047 A1 | 8/2006 | Yamashita et al. |
| 2006/0200049 A1 | 9/2006 | Leo et al. |
| 2006/0229515 A1 | 10/2006 | Sharareh et al. |
| 2007/0038116 A1 | 2/2007 | Yamanaka et al. |
| 2007/0123750 A1 | 5/2007 | Baumgartner et al. |
| 2008/0004595 A1 | 1/2008 | Viswanathan et al. |
| 2008/0033275 A1 | 2/2008 | Blank et al. |
| 2008/0097173 A1 | 4/2008 | Soyemi et al. |
| 2008/0119694 A1 | 5/2008 | Lee |
| 2008/0161774 A1 | 7/2008 | Hastings et al. |
| 2009/0005768 A1 | 1/2009 | Sharareh et al. |
| 2009/0005773 A1 | 1/2009 | Beeckler et al. |
| 2009/0013182 A1 | 1/2009 | Asghari-Kamrani et al. |
| 2009/0054908 A1 | 2/2009 | Zand et al. |
| 2009/0131802 A1 | 5/2009 | Fulghum et al. |
| 2009/0143774 A1 | 6/2009 | Uzunbajakava et al. |
| 2009/0156921 A1 | 6/2009 | Wang |
| 2009/0158852 A1 | 6/2009 | Paul et al. |
| 2010/0168548 A1 | 7/2010 | Govari et al. |
| 2010/0241100 A1 | 9/2010 | Blumenfeld et al. |
| 2010/0256461 A1 | 10/2010 | Mohamedali et al. |
| 2010/0317937 A1 | 12/2010 | Kuhn et al. |
| 2011/0040167 A1 | 2/2011 | Kim et al. |
| 2011/0054287 A1 | 3/2011 | Schultz |
| 2011/0190624 A1 | 8/2011 | Cinbis et al. |
| 2011/0313280 A1 | 12/2011 | Govari et al. |
| 2012/0265184 A1 | 10/2012 | Sliwa et al. |
| 2014/0171936 A1 | 6/2014 | Govari et al. |

FOREIGN PATENT DOCUMENTS

| | | |
|---|---|---|
| CN | 101453942 A | 6/2009 |
| CN | 101563018 A | 10/2009 |
| CN | 102309314 A | 1/2012 |
| EP | 2040059 A2 | 3/2009 |
| EP | 2742892 A1 | 6/2014 |
| JP | 2001264174 A | 9/2001 |
| JP | 2002512534 A | 4/2002 |
| JP | 2003164415 A | 6/2003 |
| JP | 2004020215 A | 1/2004 |
| JP | 2004275766 A | 10/2004 |
| JP | 2006516465 A | 7/2006 |
| JP | 2006525072 A | 11/2006 |
| JP | 2009056289 A | 3/2009 |
| JP | 2009535098 A | 10/2009 |
| JP | 2010155083 A | 7/2010 |
| JP | 2011045719 A | 3/2011 |
| JP | 2011528266 A | 11/2011 |
| JP | 2012000463 A | 1/2012 |
| JP | 2012239848 A | 12/2012 |
| WO | 0219898 A2 | 3/2002 |
| WO | 2007087529 A2 | 8/2007 |
| WO | 2009136311 A2 | 11/2009 |
| WO | 2011019838 A2 | 2/2011 |
| WO | 2012049621 A1 | 4/2012 |
| WO | 2012131577 A2 | 10/2012 |
| WO | 2012142296 A1 | 10/2012 |

OTHER PUBLICATIONS

Australian Patent Office Examination Report No. 2 for Application No. 2013270549, dated Sep. 26, 2017, 3 pages.
Australian Patent Office Examination Report No. 1 for Application No. 2011202359, dated Jul. 18, 2014, 4 pages.
Australian Patent Office Examination Report No. 1 for Application No. 2013270549, dated Jun. 30, 2017, 5 pages.
CIPO Office Action for Canadian Application No. 2742072, dated Feb. 23, 2017, 4 pages.
Demos S.G., et al., "Real Time Assessment of RF Cardiac Tissue Ablation with Optical Spectroscopy," Optics Express, Sep. 15, 2008, vol. 16 (19), pp. 15286-15296.
European Search Report for European Application No. 13197493.3, dated Feb. 28, 2014, 7 pages.
European Search Report for European Application No. 14184482.9, dated Jan. 19, 2015, 5 pages.
Extended European Search Report for European Application No. 11169931, dated Sep. 30, 2011, 7 pages.
Extended European Search Report for European Application No. 15202361.0, dated May 23, 2016, 7 pages.
First Office Action for Chinese Application No. 201110179877.8, dated Apr. 2, 2014, 3 pages.
First Office Action for Chinese Application No. 201310692975.0, dated May 26, 2017, 23 pages(with English Translation).
Halogen lamp From Wikipedia, the free encyclopedia pub, online on Oct. 10, 2012 at https://en.wikipedia.org/w/index.php?title=Halogen_lamp&oldid=516942763, 6 pages.
Incandescent light bulb From Wikipedia, the free encyclopedia pub. online on Nov. 11, 2012 at https://en.wikipedia.org/w/index.php?title=lncandescent_light_bulb&oldid=522413506, 21 pages.

(56) References Cited

OTHER PUBLICATIONS

Japanese Notification of Reasons for Refusal issued in Japanese Application No. 2011-133022, dated Feb. 3, 2015, 3 pages.
Japanese Notification of Reasons for Refusal issued in Japanese Application No. 2013-258872, dated Sep. 5, 2017, 7 pages.
Laser From Wikipedia, the free encyclopedia pub. online on Nov. 10, 2012 at https://en.wikipedia.org/w/index.php?title=Laser&oldid=522301160, 23 pages.
Light-emitting diode From Wikipedia, the free encyclopedia pub. online on Nov. 29, 2012, at https://en.wikipedia.org/w/indexphp?title=Light-emitting_diode&oldid=525554439, 27 pages.
Metal-halide lamp From Wikipedia, the free encyclopedia pub. Online on Nov. 25, 2012 at https://en.Wikipedia.org/w/index.php?title=Metal-halide_lamp&oldid=524772759, 10 pages.
Office Action for European Application No. 11169931.0, dated Apr. 24, 2012, 4 pages.
Office Action for European Application No. 13197493.3, dated Jun. 19, 2015, 3 pages.
Office Action for Japanese Application No. 2011-133022, dated Jun. 2, 2015, 2 pages.
Office Action for Japanese Application No. 2012-146541, dated May 24, 2016, 4 pages.
Office Action for Russian Application No. 2013155826, dated Dec. 13, 2017, 6 pages.
Search Report for Chinese Application No. 201110179877.8, dated Mar. 25, 2014, 3 pages.
Search Report for Chinese Application No. 201310692975.0, dated May 17, 2017, 3 pages.
Second Office Action for Chinese Application No. 201110179877.8, dated Oct. 23, 2014, 3 pages.
Swartling J., et al., "Changes in Tissue Optical Properties Due to Radio-Frequency Ablation of Myocardium," Medical & Biological Engineering & Computing, Jul. 2003, vol. 41(4), pp. 403-409.
Third Office Action for Chinese Application No. 201110179877.8, dated Apr. 20, 2015, 3 pages.
Vertical-cavity surface-emitting laser From Wikipedia, the free encyclopedia; Pub, online on Nov. 6, 2012 at https://en.Wikipedia.org/w/i ndex. php?title= Vertical-cavity_ surface-emitting_laser &old id=521730098, 4 pages.

* cited by examiner

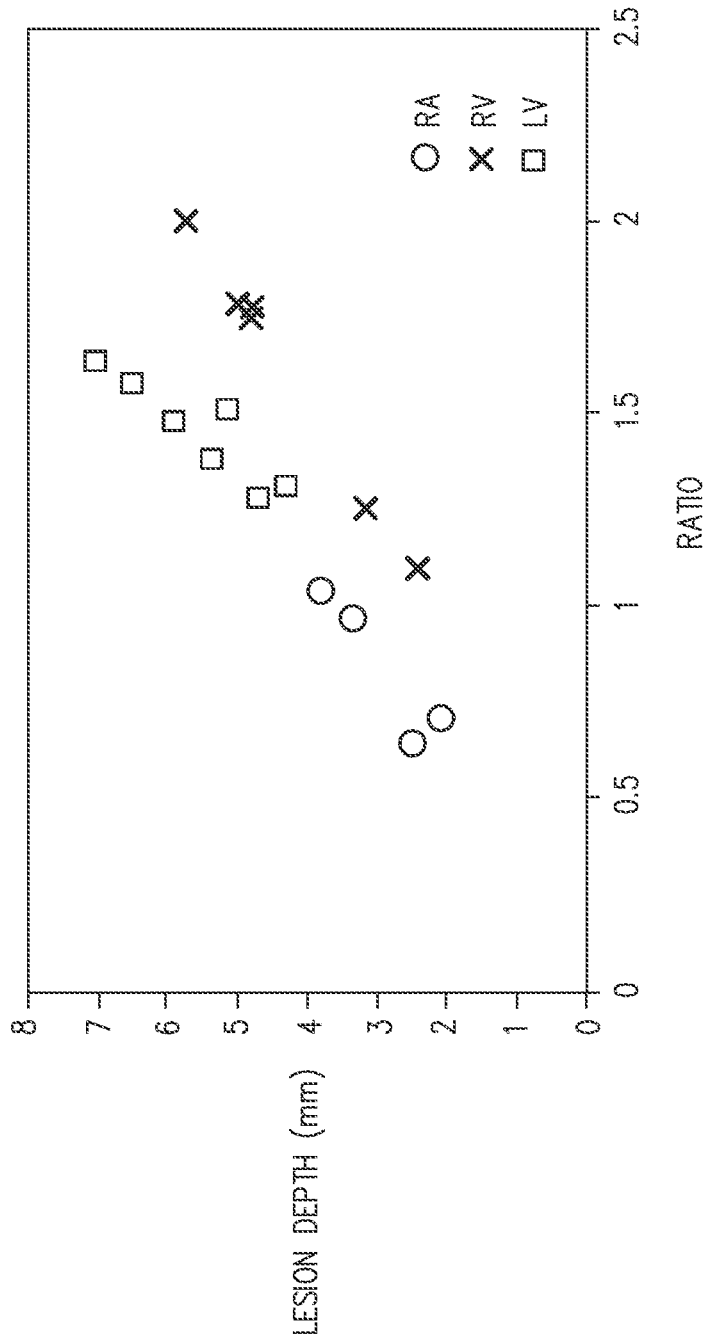

SPECTRAL SENSING OF ABLATION

CROSS-REFERENCE TO RELATED APPLICATIONS

The present application is a Continuation under U.S.C. § 120 of U.S. patent application Ser. No. 14/585,135, filed Dec. 29, 2014, which is a continuation-in-part of U.S. patent application Ser. No. 13/716,517, filed Dec. 17, 2012 (published as U.S. Patent Application Publication 2014/0171806), which is a continuation-in-part of U.S. patent application Ser. No. 12/816,492, filed Jun. 16, 2010. The entire contents of these applications are incorporated by reference herein in their entirety.

FIELD OF THE INVENTION

The present invention relates generally to invasive medical devices and methods of treatment, and particularly to assessing ablation of tissue within the body.

BACKGROUND

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

Various methods for monitoring ablation treatments are known in the art. For example, U.S. Pat. No. 7,001,383, whose disclosure is incorporated herein by reference, describes real-time monitoring and mapping of ablation lesion formation in the heart. The disclosed method includes applying a local treatment to the heart at a plurality of sites designated for ablation. At each respective site, a parameter is sensed that is indicative of a level of ablation at the site. The method preferably includes displaying a map of the heart, and designating, on the map, during the ablation procedure, indications of the respective levels of ablation at the sites, responsive to the respective sensed parameters.

U.S. Patent Application Publication 2014/0171936, whose disclosure is incorporated herein by reference, describes a catheter having an irrigated tip with temperature sensors and an optical fiber array. The catheter comprises an insertion tube having a distal end configured for insertion into proximity with tissue in a body of a patient and containing a lumen having an electrical conductor for conveying electrical energy to the tissue. A conductive cap is attached to the distal end of the insertion tube and is coupled electrically to the electrical conductor. A multiplicity of optical fibers are contained within the insertion tube, each fiber terminating in proximity to the outer surface of the cap, and being configured to convey optical radiation to and from the tissue while the electrical energy is being conveyed to the tissue.

U.S. Pat. No. 8,147,484 describes a system and method that enable real-time optical measurements of tissue reflection spectral characteristics while performing ablation. The method involves the radiation of tissue and recapturing of light from the tissue to monitor changes in the reflected optical intensity as an indicator of steam formation in the tissue for prevention of steam pop. The system includes a catheter adapted to collect light reflected from tissue undergoing ablation, a detection component that identifies and separates constituent wavelengths of collected light, a quantification apparatus for generating measured light intensity data for the collected light, and a processor that analyzes the measured light intensity data in relation to time. A measured reflectance spectral intensity (MRSI) versus time is analyzed, wherein observation is made as to whether the MRSI initially increases in a specified time period followed by a decrease at a specified rate in the MRSI. If there is no decrease in the MRSI, then delivery of ablation energy to tissue continues. However, if there is a decrease in the MRSI within a specified time and at a specified rate, then the method infers the formation of a steam pocket and decreases or discontinues the delivery of ablative energy to tissue.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY

Embodiments of the present invention that are described hereinbelow provide apparatus and methods that can be used in assessing tissue undergoing an ablation procedure.

There is therefore provided, in accordance with an embodiment of the present invention, a method for tissue assessment, which includes ablating tissue at a site within a body of a living subject using an invasive probe applied to the site. At a first stage in ablation of the tissue, first measurements are made of scattered light intensities from the site at a plurality of different wavelengths. At a second stage in the ablation of the tissue, subsequent to the first stage, second measurements are made of the scattered light intensities from the site at the plurality of different wavelengths. Progress of the ablation is assessed by computing different, respective measures of change in the scattered light intensities at the different wavelengths occurring between the first and second measurements, and comparing the respective measures.

In a disclosed embodiment, ablating the tissue includes ablating myocardial tissue in a heart of the subject, typically by inserting a catheter into the body and applying energy to the tissue via the catheter.

In some embodiments, making the first and second measurements includes directing light toward the site from an emitter in the probe, and collecting the light scattered from the tissue using a receiver in the probe. In a disclosed embodiment, the emitter and the receiver include at least one optical fiber, which extends through the probe between an optical port in proximity to the site at a distal end of the probe and an optical measurement module coupled to a proximal end of the probe.

In the disclosed embodiments, the plurality of the different wavelengths includes a first wavelength in a visible light range and a second wavelength in an infrared light range. Typically, the first wavelength is between 600 and 700 nm, and the second wavelength is between 700 and 800 nm. In one embodiment, the first wavelength is between 630 and 670 nm, the second wavelength is between 750 and 790 nm, and the plurality of the different wavelengths includes a third wavelength between 670 and 710 nm.

In a disclosed embodiment, computing the different, respective measures includes computing first, second and third ratios between the first and second measurements of the scattered light intensities at the first, second and third wavelengths, respectively, and comparing the respective measures includes evaluating a mathematical relation between first, second and third ratios in order to assess the progress of the ablation. Typically, evaluating the mathematical relation includes estimating a size of a lesion created by the ablation at the site based on a product of the second and third ratios divided by the first ratio.

More generally, computing the different, respective measures includes computing at least first and second ratios between the first and second measurements of the scattered light intensities at the first and second wavelengths, and assessing the progress includes estimating a size of a lesion created by the ablation at the site based on a comparison between the first and second ratios.

There is also provided, in accordance with an embodiment of the present invention, medical apparatus, including an invasive probe, which is configured to be inserted into a body of a living subject, to direct light at a plurality of different wavelengths toward a treatment site within the body and to receive the light scattered from the site. An optical module is coupled to the invasive probe so as to make, at a first stage in ablation of tissue at the treatment site, first measurements of scattered light intensities from the site at the plurality of different wavelengths, and to make, at a second stage in the ablation of the tissue, subsequent to the first stage, second measurements of the scattered light intensities from the site at the plurality of different wavelengths. A processor is configured to assess a progress of the ablation by computing different, respective measures of change in the scattered light intensities at the different wavelengths occurring between the first and second measurements, and comparing the respective measures.

The present invention will be more fully understood from the following detailed description of the embodiments thereof, taken together with the drawings in which:

BRIEF DESCRIPTION OF THE DRAWINGS

FIG. 7 is a schematic plot comparing ablation lesion depth to a ratio of scattered light intensities over multiple lesions, in accordance with an embodiment of the present invention.

DETAILED DESCRIPTION OF EMBODIMENTS

One of the challenges in ablation of myocardial tissue is to know when to stop the treatment at a given site: Applying too little energy may result in creation of only a superficial lesion, which does not achieve the desired therapeutic purpose, whereas applying too much energy can cause excessive tissue damage and even perforation. It is therefore desirable to assess the size (and particularly the depth) of the lesion that has been created at any point during the ablation procedure, and thus to terminate the procedure when it has achieved the desired lesion size.

The inventors have discovered in this regard that certain optical spectral properties of myocardial tissue change during ablation, and that these properties give a good indication of lesion size. Specifically, the inventors have found that the intensity of scattered light changes by different degrees at different wavelengths during ablation, particularly at selected wavelengths in the red and near infrared ranges. The relation between the relative scattering changes at different wavelengths, which may be expressed as a quotient of the ratios of pre- and post-ablation scattering intensities measured at the different wavelengths, correlates well with lesion depth.

Thus, in the embodiments that are described hereinbelow, an invasive probe is applied to a site in the body at which tissue is to be ablated. The probe is used to make measurements of scattered light intensities from the site at a number of different wavelengths at different stages in the ablation process. A processor computes different, respective measures of change in the scattered light intensities at the different wavelengths that occur between the first and second measurements, and compares the respective measures in order to assess the progress of the ablation. Such measurements may be made and compared, for example, before, during, and at the conclusion of the process, and provide an estimate of the lesion size, and specifically the lesion depth, at each stage.

The embodiments described below relate to ablation of myocardial tissue using a probe in the form of a catheter, which applies energy (such as electrical energy) in order to ablate the tissue. The catheter contains one or more optical fibers, with optical ports at the distal end of the catheter through which light at different wavelengths is directed toward the tissue and scattered light is received, for purposes of spectroscopic comparison. Alternatively, however, the principles of the present invention may be applied using probes and optical receivers and transmitters of other types, in ablation of both myocardial tissue and other types of tissue, using any suitable ablation technique that is known in the art.

Figure 1:
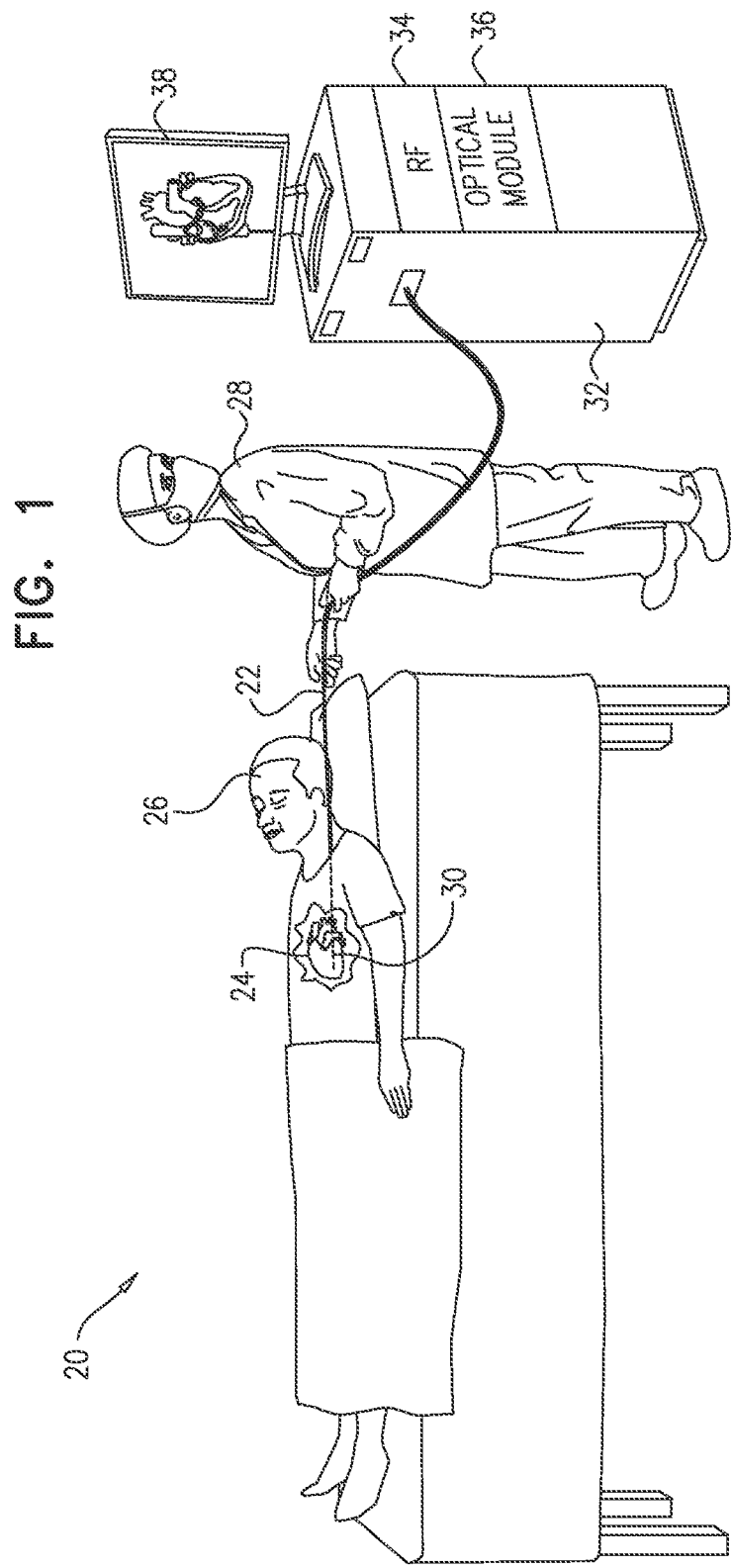
FIG. 1 is a schematic pictorial illustration of a system for intracardiac ablation, in accordance with an embodiment of the present invention.

FIG. 1 is a schematic pictorial illustration of a system 20 for cardiac ablation treatment, in accordance with an embodiment of the present invention. An operator (such as an interventional cardiologist) inserts a catheter 22 via the vascular system of a patient 26 into a chamber of the patient's heart 24. For example, to treat atrial fibrillation, the operator may advance the catheter into the left atrium and bring a distal end 30 of the catheter into contact with myocardial tissue that is to be ablated.

Catheter 22 is connected at its proximal end to a console 32, which is controlled by operator 28 to apply and monitor the desired treatment. Console 32 in this embodiment comprises a radio frequency (RF) energy generator 34, which supplies electrical power via catheter 22 to distal end 30 in order to ablate the target tissue. An optical module 36 provides optical radiation, typically from one or more light sources, which may comprise lasers, incandescent lamps, arc lamps, or light emitting diodes (LEDs), for transmission from distal end 30 to the target tissue. Module 36 receives and analyzes optical radiation returning from the target tissue and acquired at the distal end, as described below. On the basis of these results, console 32 may control the power applied by RF energy generator 34, as well as other aspects of the ablation procedure, either automatically or in response to inputs by operator 28. For this latter purpose, console 32 typically presents the relevant measurement results on a display 38.

Console 32 may also receive and track signals from catheter 22 relating to parameters such as the location and of distal end 30 and the force exerted by the distal end on the tissue. An irrigation pump in console 32 typically supplies a cooling fluid, such as saline solution, through catheter 22 to irrigate distal end 30. System 20 may be based in part on the CARTO system, produced by Biosense Webster Inc. (Diamond Bar, Calif.), which provides these sorts of facilities to support navigation and control of catheter 22. These optional features of system 20, however, are beyond the scope of the present description and are omitted from the figures for the sake of simplicity.

Figure 2:
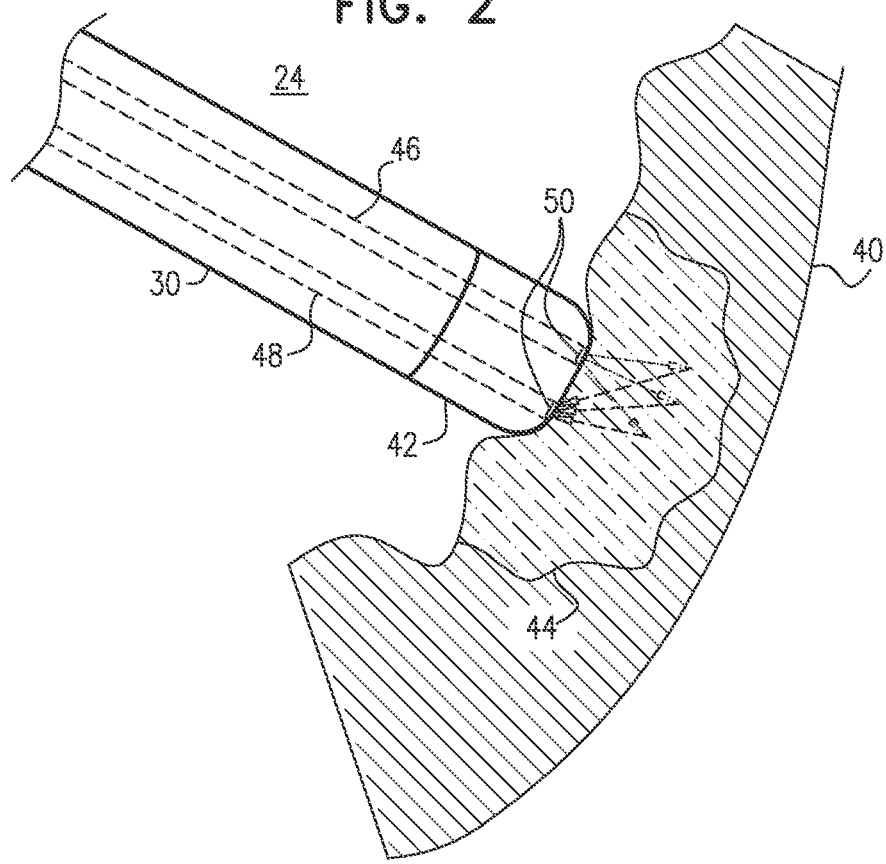
FIG. 2 is a schematic detail view of a catheter in contact with myocardial tissue during an ablation procedure, in accordance with an embodiment of the present invention.

FIG. 2 is a schematic detail view showing distal end 30 of catheter 22 in contact with myocardial tissue 40 during an ablation procedure, in accordance with an embodiment of the present invention. Catheter 22 has a conductive cap 42 at its distal end. Typically, cap 42 comprises a biocompatible metal suitable to serve as an ablation electrode, such as gold, palladium, platinum, or an alloy of these materials, for example. An electrical conductor (not shown) in catheter 22 conveys electrical energy from RF generator 34, through catheter 22, to cap 42, in order to energize the cap to ablate myocardial tissue with which the cap is in contact, thus creating a lesion 44. Further details of a catheter and cap having these features are described, for example, in the above-mentioned U.S. Patent Application Publication 2014/0171936.

Catheter 22 comprises optical fibers 46, 48, which extend through the catheter between optical module 36 and respective optical ports 50 opening through cap 42 in distal end 30. In the pictured example, fiber 46 emits light into the ablation site, while fiber 48 receives the light that is scattered from the tissue and returns it to the optical module. The term "light," in the context of the present description and in the claims, refers to optical radiation in any wavelength band, including visible, infrared, and/or ultraviolet radiation.

Although two fibers 46, 48 and corresponding ports 50 are shown in FIG. 2, catheter 22 may alternatively comprise a smaller or large number of optical fibers, as well as light emitters and receivers of other sorts. For example, miniature light sources and detectors, such as suitable LEDs and photodiodes, may be embedded in the catheter tip in order to emit and sense received light. Additionally or alternatively, the catheter may comprise lenses and/or other types of transmission and collection optics.

Figure 3:
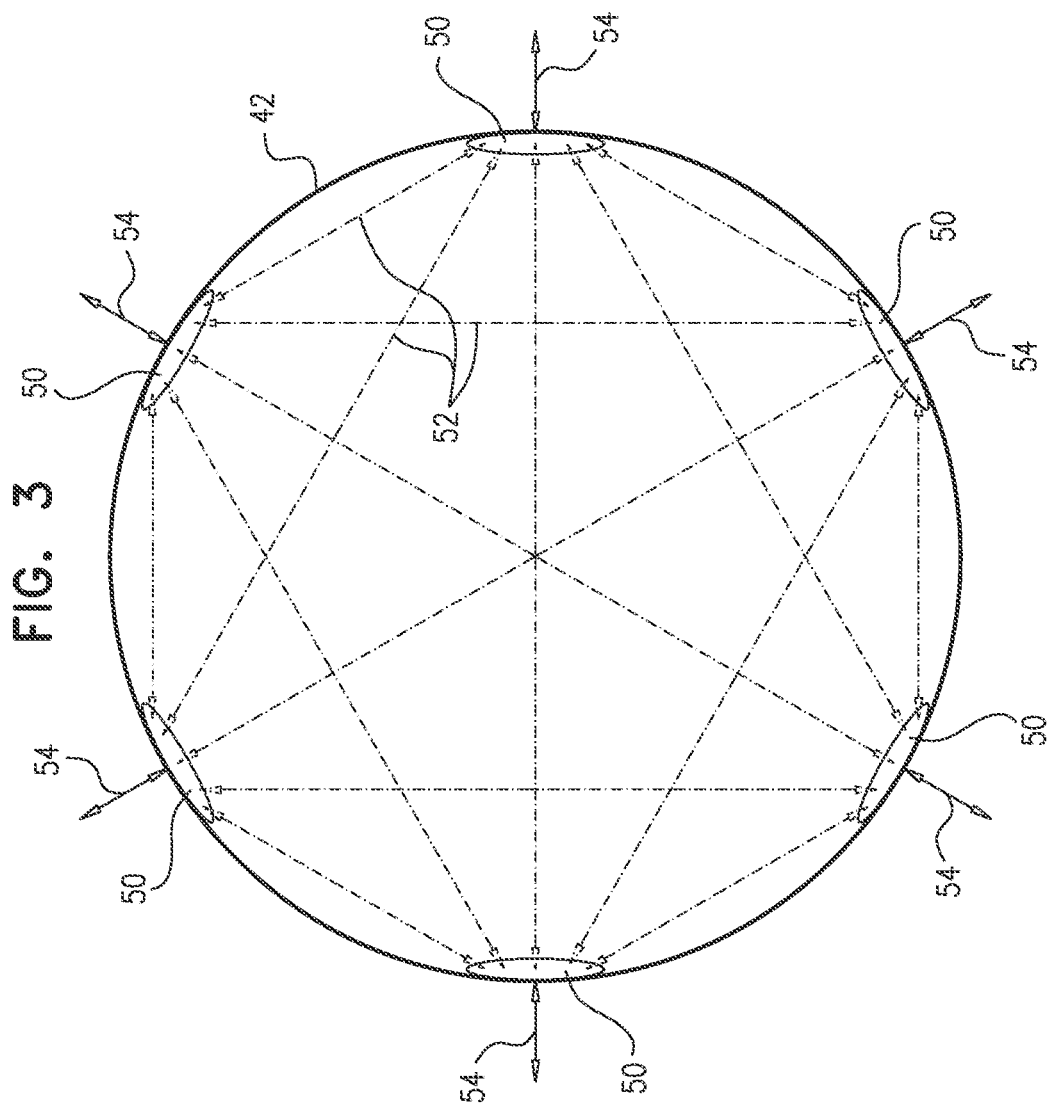
FIG. 3 is a schematic end view of the distal tip of a catheter with optical sensing capabilities, in accordance with an embodiment of the present invention.

FIG. 3 is a schematic end view of cap 42 at distal end 30 of catheter 22, in accordance with an embodiment of the present invention. In this view, it is assumed that six optical fibers passing through the catheter, like fibers 46 and 48 in FIG. 2, terminate at respective windows 50 at different locations in cap 42. This arrangement enables different combinations of fibers to be used in probing different locations within lesion 44. The available probing paths include single-window paths 54, in which the light emitted from a given window 50 returns to the same window, so that the same fiber serves as emitter and receiver. Inter-window paths 52 define configurations in which light from a given window returns to a different window.

The scattered light received from any given path 52, 54 or group of paths depends on characteristics of tissue in the path or group of paths. Longer paths tend to probe deeper into tissue 40. The inventors have found that for purposes of the measurements described hereinbelow, it is useful to illuminate the tissue through one of windows 50 and receive the scattered radiation via multiple paths 52 simultaneously, for example through all of the other windows. This approach gives good coverage of the region of lesion 44 and high signal/noise ratio. Alternative, other paths and combinations of paths may be used in order to enhance spatial resolution.

Figure 4:
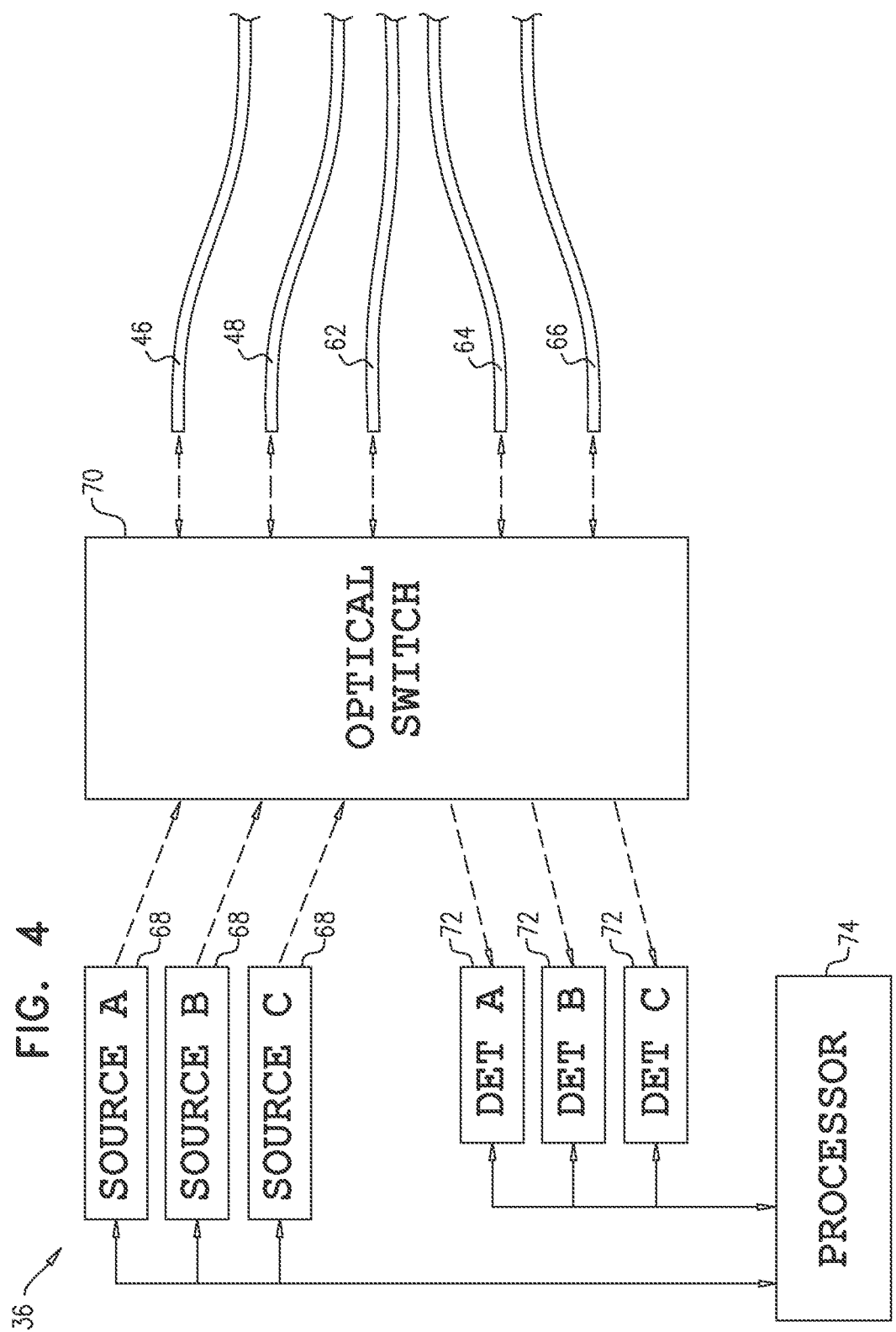
FIG. 4 is a block diagram that schematically illustrates an optical module, in accordance with an embodiment of the present invention.

FIG. 4 is a block diagram that schematically shows details of optical module 36 in console 32, in accordance with an embodiment of the present invention. One or more radiation sources 68 emit optical radiation. An optical switch 70 is set to select one or more of optical fibers 46, 48, 62, 64, 66, . . . , running through catheter 22, that are to receive the emitted radiation and transmit the radiation to the tissue at the ablation site. Switch 70 likewise routes the scattered radiation returned from the ablation site by one or more of the optical fibers to one or more detectors 72. Optical switch 70 may comprise, for example, a suitable arrangement of movable reflectors, as well as focusing elements, for directing light along the desired paths. Alternatively or additionally, switch 70 may comprise a chopper wheel and beam splitters that allow only one source at a time to couple to the fibers, while allowing the detectors to receive light from all fibers. Optionally, switch 70 may also include optical filters and/or other wavelength-selective or dispersive elements as an aid to wavelength-resolved measurements. Various designs of optical module 36 that support the measurement schemes described herein will be apparent to those skilled in the art after reading the present description, and all such designs are considered to be within the scope of the present invention.

In some embodiments, each of sources 68 comprises a narrowband optical emitter, such as a suitable LED or laser diode, operating at a particular measurement wavelength. Possible criteria for selecting these wavelengths are illustrated in the figures that follow. For example, source A may comprise a red light source, while source B comprises an infrared source. More specifically, source A typically emits light at a wavelength between 600 and 700 nm, while source B emits light at a wavelength between 700 and 800 nm. In one advantageous implementation, source A emits light at a wavelength between 630 and 670 nm, while source B emits light at a wavelength between 750 and 790 nm, and source C emits light at a third wavelength between 670 and 710 nm. The usefulness of these particular wavelength ranges in estimating lesion size is explained further hereinbelow.

Alternatively or additionally, one or more of sources 68 may comprise a broadband source, which typically emits light over a range of wavelengths in at least the infrared and visible ranges. In this case, optical switch 70 may comprise a dispersive element, such as a grating or prism, which separates the different wavelength components of the scattered light received from the ablation site among the different detectors 72, so that each detector receives a different wavelength or wavelength range, such as the red and infrared ranges mentioned above. The measurement results shown in FIGS. 5 and 6 were obtained in this manner.

Figure 5:
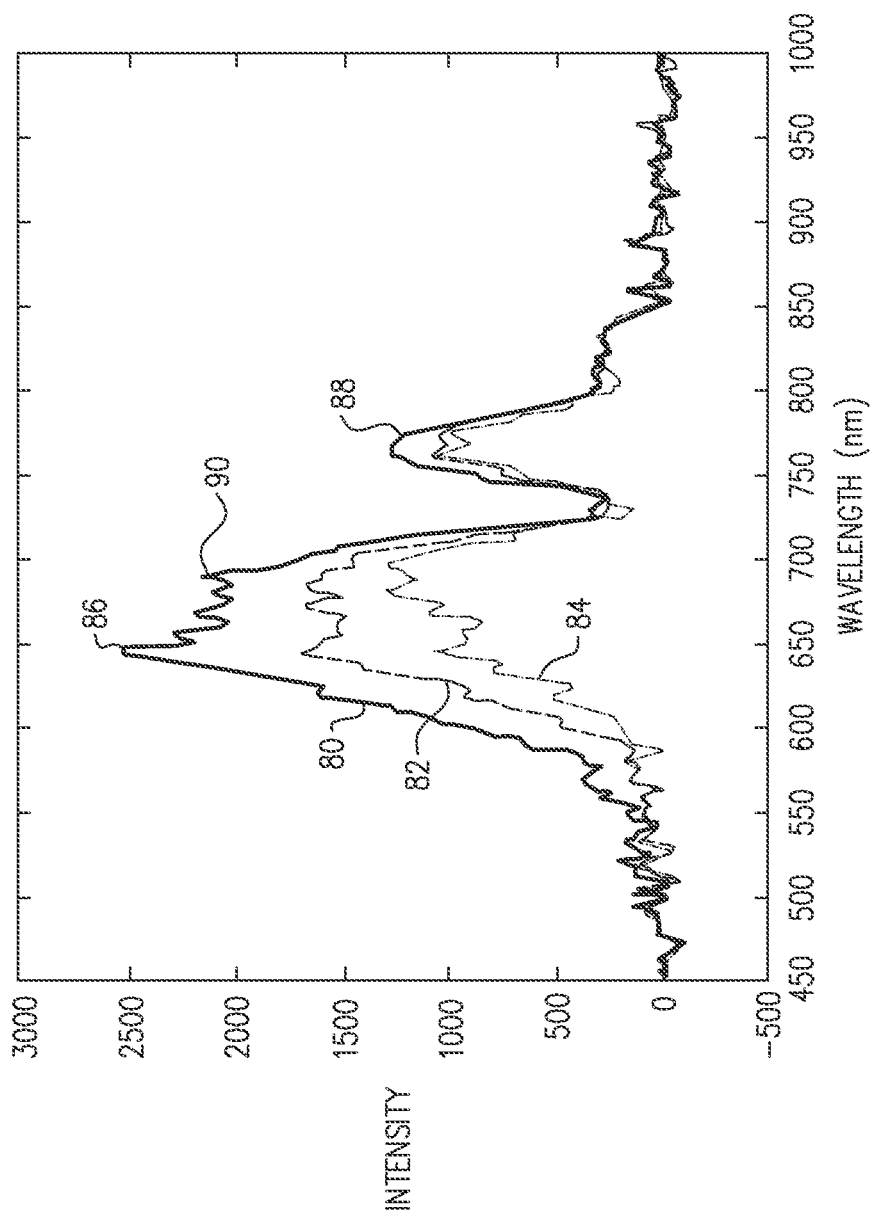
FIGS. 5 and 6 are schematic spectral plots of scattered light intensity from ablation sites at successive stages in ablation procedures at the sites, in accordance with an embodiment of the present invention.
Figure 6:
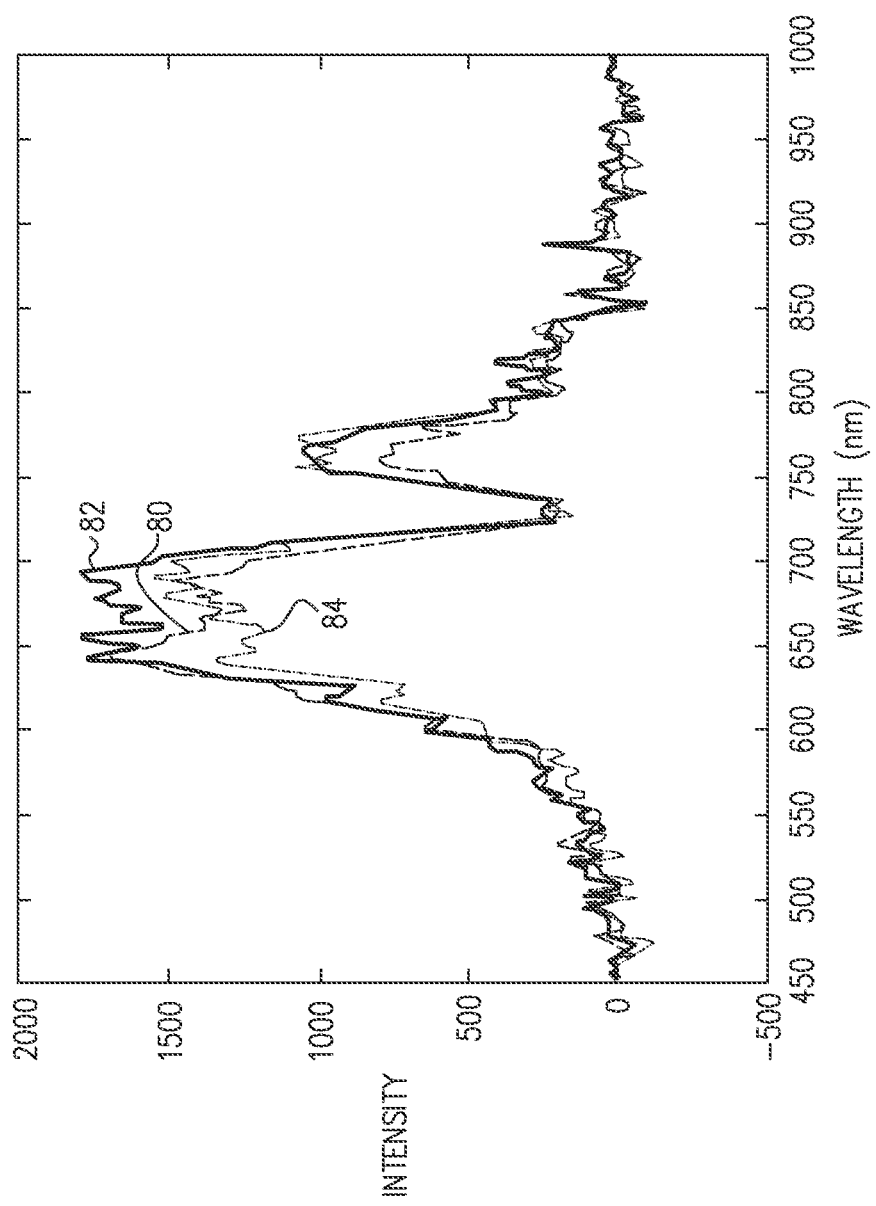

FIGS. 5 and 6 are schematic spectral plots of scattered light intensity from ablation sites at successive stages in ablation procedures at the sites, in accordance with an embodiment of the present invention. The plots show spectral intensity as a function of wavelength at three different points in time during two different ablation procedures (selected from among 17 lesions created in procedures performed on experimental animals). The measurements were made using a system and catheter similar to those illustrated and described above. In each case, broadband radiation was delivered to the ablation site through one of the optical fibers, and the scattered radiation was received through one or more other fibers and measured spectroscopically.

Three spectroscopic curves are shown in each figure: a pre-ablation spectrum 80, an intermediate spectrum 82 captured during the ablation procedure, and a post-ablation spectrum 84. The spectra consistently exhibited the sort of bi-modal structure that is shown in FIGS. 5 and 6, with a red band-edge peak 86 in the range of 643-650 nm and a near infrared peak 88 at 765-772 nm. The intensities at peaks 86 and 88 was measured, along with an intermediate peak 90 at the intermediate band edge located at 690-698 nm (on the border between red and infrared). In general, the intensity decreased during the ablation process over the entire spectral band of interest (between about 600 and 800 nm) and could thus give an indication of the ablation in progress.

The inventors found, however, that the ratios between the post- and pre-ablation measurements of the scattered light intensities at peaks 86 and 88 gave a more reliable estimate of the size of the lesion created by the ablation, and that comparison between these ratios—which are generally different from one another—gives a useful indication of lesion depth. The estimate is improved still further when the ratio of post- and pre-ablation measurements at peak 90 is also evaluated, and a mathematical relation is evaluated between the ratios at the three peaks.

In particular, the product of the ratios at peaks 88 and 90 divided by the ratio at peak 86 gives the overall ratio value L, which was found experimentally to increase in proportion to the lesion depth:

$$L = \frac{(E_2/S_2)(E_3/S_3)}{(E_1/S_1)}$$

In this expression, $S_j$ is the pre-ablation intensity at peak 86 ($S_1$), peak 88 ($S_2$), or peak 90 ($S_3$), while $E_j$ is the corresponding intensity at a subsequent stage of the ablation (which may be an intermediate stage or completion of the procedure). In other words, deeper ablation is characterized by a large drop in the spectral intensity at the infrared and intermediate wavelengths relative to the drop at the red wavelength. For example, for the curves shown in FIG. 5, L=1.32, while the actual lesion depth (measured following dissection of the heart) was 3.12 mm; whereas for the curves shown in FIG. 6, L=2.01, and the measured lesion depth was 5.71 mm.

FIG. 7 is a schematic plot comparing ablation lesion depth (in millimeters) to the ratio value L over multiple lesions, in accordance with an embodiment of the present invention. The relation between L and the lesion depth varied among different chambers of the heart, and therefore, different symbols are used to indicate the results measured in the right atrium (RA), right ventricle (RV) and left ventricle (LV). In all cases, however, the lesion depth scaled clearly, in a roughly linear manner, with the ratio value L.

To apply these principles in system 20, optical module 36 measures the spectral intensity of the light scattered from the ablation site, and processor 74 computes L during and after ablation. Processor 74 typically outputs this value as an indication to operator 28. Additionally or alternatively, the processor may use the ratio value, typically in conjunction with other sensed parameters, in controlling the application of ablation energy autonomously or semi-autonomously.

Although the experimental results presented above make use of certain particular wavelength ranges, relations between spectral intensities at other choices of red and near-infrared wavelengths may be used to similar effect. It should be understood in this regard that a ratio between a pair of successive measurements or a relation between dividend and divisor may be expressed equivalently as the quotient of the first value divided by the second or the second value divided by the first. Furthermore, although ratios are used in the embodiments described above in comparing different spectral intensity values, other arithmetic operations, such as subtraction, may alternatively be applied in comparing spectral values and computing quantitative measures of change.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method of ablating tissue, comprising:
    beginning an ablation procedure to create a lesion at the tissue at a site within a body of a living subject using an invasive probe applied to the site;
    at a first stage in the ablation procedure, making first measurements of scattered light intensities from the site at a first wavelength, a second wavelength, and a third wavelength;
    at a second stage in the ablation procedure, subsequent to the first stage, making second measurements of the scattered light intensities from the site at the first wavelength, the second wavelength, and the third wavelength;
    computing a first ratio between the first measurement and the second measurement at the first wavelength, computing a second ratio between the first measurement and the second measurement at the second wavelength, and computing a third ratio between the first measurement and the second measurement at the third wavelength;
    dividing a product of the second and third ratios by the first ratio to determine an overall ratio value;
    based on the overall ratio value, determining an estimated size of the lesion;
    comparing the estimated size of the lesion to a desired lesion size;
    determining whether the ablation procedure has achieved the desired lesion size; and
    terminating the ablation procedure upon determining that the ablation procedure has achieved the desired lesion size.

2. The method according to claim 1, in which the tissue site comprises a myocardial tissue in a heart of the subject.

3. The method according to claim 1, in which making the first and second measurements comprises directing light toward the site from an emitter in the probe, and collecting the light scattered from the tissue using a receiver in the probe.

4. The method according to claim 3, in which the probe includes a cap having an optical port disposed at a distal end of the probe, and the emitter and the receiver comprise at least one optical fiber, which extends through the probe and terminates at the optical port.

5. The method according to claim 1, in which the first wavelength comprises a visible-light wavelength and the second wavelength comprises an infrared-light wavelength.

6. The method according to claim 5, in which the third wavelength comprises a visible-light wavelength greater than the first wavelength.

7. The method according to claim 5, in which the first wavelength is between 600 nm and 700 nm, and the second wavelength is between 700 nm and 800 nm.

8. The method according to claim 7, in which the third wavelength is between 670 nm and 710 nm.

9. The method according to claim 6, further comprising controlling an application of ablation energy based on the overall ratio value.

10. The method according to claim 9, in which the controlling step includes automatically controlling the application of ablation energy.

11. The method according to claim 1, in which the first intensity measurement comprises a first peak and the second intensity measurement comprises a second peak.

12. A medical apparatus, comprising:
an invasive probe including a cap configured to ablate a tissue disposed at a distal end of the invasive probe, and an optical fiber extending through the probe and terminating at an optical port disposed through the cap;
a radiation source connected to the optical fiber;
a detector connected to the optical fiber; and
a processor connected to the radiation source and the detector, and configured to:
begin an ablation procedure to create a lesion at a tissue site;
receive a first intensity measurement and a second intensity measurement from the detector;
compute a first ratio between the first intensity measurement and the second intensity measurement at a first wavelength, a second ratio between the first intensity measurement and the second intensity measurement at a second wavelength, and a third ratio between the first intensity measurement and the second intensity measurement at a third wavelength;
divide a product of the second and third ratios by the first ratio to determine an overall ratio value;
based on the overall ratio value, determine an estimated size of the lesion;
compare the estimated size of the lesion to a desired lesion size;
determine whether the ablation procedure has achieved the desired lesion size; and
terminate the ablation procedure upon determining that the ablation procedure has achieved the desired lesion size.

13. The apparatus according to claim 12, in which the tissue site comprises a myocardial tissue in a heart of the subject.

14. The apparatus according to claim 12, in which the first intensity measurement comprises a first peak and the second intensity measurement comprises a second peak.

15. The apparatus according to claim 12, in which the first wavelength comprises a visible-light wavelength and the second wavelength comprises an infrared-light wavelength.

16. The apparatus according to claim 15, in which the third wavelength comprises a visible-light wavelength greater than the first wavelength.

17. The apparatus according to claim 15, in which the first wavelength is between 600 nm and 700 nm, and the second wavelength is between 700 nm and 800 nm.

18. The apparatus according to claim 17, in which the third wavelength is between 670 nm and 710 nm.

19. The apparatus according to claim 16, in which the processor is further configured to control an application of ablation energy based on the overall ratio value.

20. The apparatus according to claim 19, in which the processor is further configured to control the application of ablation energy automatically.

* * * * *